United States Patent [19]

Huber

[11] 4,122,157

[45] Oct. 24, 1978

[54] NITROFURANTOIN SUSTAINED RELEASE TABLET

[75] Inventor: Harold E. Huber, Cincinnati, Ohio

[73] Assignee: Richardson-Merrell Inc., Wilton, Conn.

[21] Appl. No.: 774,279

[22] Filed: Mar. 4, 1977

[51] Int. Cl.$^2$ ............................................. A61K 9/24
[52] U.S. Cl. ...................................... 424/21; 424/19; 424/22
[58] Field of Search .................................... 424/19–22

[56] References Cited

U.S. PATENT DOCUMENTS 3,065,143  11/1962  Christenson et al. ................... 424/22
3,558,768  1/1971   Klippez ................................... 424/21
3,773,920  1/1973   Nakamoto et al. ...................... 424/19

FOREIGN PATENT DOCUMENTS 2,133,122  1/1972   Fed. Rep. of Germany.
2,050,701  5/1971   Fed. Rep. of Germany.
2,404,609  9/1974   Fed. Rep. of Germany.
7,343,848  12/1973  Japan.
1,279,214  6/1972   United Kingdom.

Primary Examiner—Shep K. Rose
Attorney, Agent, or Firm—William J. Stein; Eugene O. Retter; George W. Rauchfuss, Jr.

[57] ABSTRACT

A pharmaceutically acceptable layered tablet containing nitrofurantoin in substained release form.

5 Claims, No Drawings

NITROFURANTOIN SUSTAINED RELEASE TABLET

BACKGROUND OF THE INVENTION

Nitrofurantoin, chemically known as 1-[(5-nitrofurfurylidene)amino]hydantoin, is a well-known antibacterial agent for the treatment of urinary tract infections. The drug is remarkably well tolerated in humans, the most frequent adverse reactions involving complaints of anorexia, nausea and emesis.

Numerous attempts have been made to alleviate these undesirable side effects and at the same time provide a dosage form requiring less frequent administration that is essentially biologically equivalent to the standard 100 mg tablet of nitrofurantoin administered four times daily.

Attempts to minimize these side-effects such as diet control, the combination of nitrofurantoin with other substances, enteric coated tablets and reduced dosage regimens have not proven successful. U.S. Pat. No. 3,401,221 discloses crystals of nitrofurantoin, substantially cubic in form that are capable of passing through a 50 U.S. mesh screen but not through a 400 U.S. mesh screen. Administration of the drug in the form of such large crystals is stated to reduce in some degree the nausea and emesis side-effects obtained. There still remain, however, a relatively minor, but nevertheless substantial, number of patients who are deprived of the benefits of this useful drug because of these undesirable side-effects.

Additionally, in order to improve upon the efficacy of nitrofurantoin in the treatment of urinary infections, efforts must be directed to provide more of a prompt physiologic disposition of the drug at the situs of infection, i.e., a more rapid urinary excretion of the unaltered drug in effective concentrations and amounts upon oral administration. The administration of nitrofurantoin having a relatively large crystal size so as to reduce the incidence of nausea and emesis, concomitantly results in delayed urinary excretion and reduced urinary concentrations of the unaltered drug.

SUMMARY OF THE INVENTION

This invention relates to a novel compressed pharmaceutical tablet containing nitrofurantoin. More particularly, this invention relates to a tablet comprising two discrete portions, a rapid release portion and a slow release portion, each portion containing a specific quantity of specially prepared nitrofurantoin. Still more particularly, the present invention relates to a compressed pharmaceutical tablet comprising a fast release portion comprising from 3 to 9% of total tablet weight of micronized nitrofurantoin and from 8 to 46% of total tablet weight of inert pharmaceutical excipients; and a slow release portion comprising from 9 to 27% of total tablet weight of micronized nitrofurantoin, from 14 to 42% of total tablet weight of hydroxypropyl methylcellulose having a viscosity of from 90 to 120 cps, and from 8 to 42% of total tablet weight of inert pharmaceutical excipients. For purposes of the present invention, the hydroxypropyl methylcellulose contained in the slow release portion is not considered an inert pharmaceutical excipient and is treated separately.

In addition, the present invention relates to a method of treating urinary tract infections in humans which comprises the oral administration of a tablet of the present invention not more than three times daily.

DETAILED DESCRIPTION OF THE INVENTION

In order to achieve therapeutic efficacy, nitrofurantoin is most frequently administered in the form of a 100 mg oral tablet, at appropriate intervals four times daily. The result is a series of four undulatory urinary excretion profiles in which the maximum amounts of nitrofurantoin excreted, above and beyond that required to achieve therapeutic effect, is related to the untoward side-effects experienced with the drug. By carefully controlling the rate of nitrofurantoin absorption, so as to avoid excessive drug absorption while yet maintaining effective urinary concentrations of the drug, the undesirable side-effects of nausea, emesis or anorexia can be avoided.

Previous attempts have been made, to administer nitrofurantoin in a slow release or sustained release form in order to minimize these undesirable side-effects. Unfortunately, as the length of time for drug dissolution is extended, the total amount of unchanged drug excreted in the urine diminishes, thereby requiring the administration of increased amounts of drug with a concomitant increase of side-effects. Moreover, the use of these various slow release forms results in an approximate 2 to 3 hour delay in the appearance of the drug in the urine. Thus, it would be highly desirable to be able to administer a suitable pharmaceutical formulation containing nitrofurantoin, which would both hasten and at the same time prolong the appearance of the drug at therapeutic concentrations in the urinary system, while still maintaining absorption concentrations of the drug below a level that will elicit these undesirable side-effects. In addition, it would be highly desirable to orally administer a tablet in dosage unit form only twice or, at the most, three times daily in lieu of the present mode of administration which requires the administration of a tablet four times daily.

Following a long series of investigations, I have discovered a novel compressed pharmaceutical tablet suitable for oral administration that both reduces the undesirable side-effects associated with nitrofurantoin administration and at the same time provides an earlier and more rapid absorption and urinary excretion of the drug than has heretofore been obtained. Moreover, administration of the particular dosage unit form herein described requires only two or, at the most, three daily doses, in contradistinction to the tablets currently available which must be administered four times per day. The administration of only two or three daily dosages is highly desired inasmuch as it enhances patient compliance during the course of treatment.

The tablets of the present invention contain two separate and discrete portions — a rapid release portion and a slow release portion. The rapid and slow release portions of the tablet can be laminated or otherwise compounded to provide a dosage form that provides rapid initial urinary levels and the continuous or sustained levels of nitrofurantoin desired. A preferred tablet embodiment is in the form of a layered tablet. The tablet can also be manufactured as an inner or core portion and an outer dosage component, the latter in the form of an envelope surrounding the former. Alternatively, the rapid release and slow release granules may be separately colored and compressed as a variegated color tablet. The term tablet is intended to encompass any compressed form of tablet, as for example, chewable, soluble, effervescent, buccal and sublingual tablets.

The rapid release portion of the tablet comprises from about 3% to about 9% of the total tablet weight of micronized nitrofurantoin. To obtain micronized nitrofurantoin, the drug is pulverized using a fluid energy mill or micronizer to a particule size ranging in general from about 1 to about 25 microns in diameter. Preferably, the major portion of micronized nitrofurantoin has a particle size of one micron or less. Nitrofurantoin can be directly micronized. However, it has been found expedient to micronize the drug with a carrier, such as lactose, starch or calcium carbonate in order to avoid clogging or clumping of the product, and to maintain nitrofurantoin homogeneously dispersed throughout the mixture. The preferred carrier of choice is lactose.

The remaining rapid release portion comprises from about 8% to about 46% of total tablet weight of inert pharmaceutical excipients. These pharmaceutical excipients include diluents such as calcium phosphate, calcium sulfate, lactose, kaolin, manitol, crystalline sorbitol or powdered sugar which serve to increase tablet bulk suitable for compression. A binder is generally also employed to impart a cohesiveness to the tablet formulation and insure tablet integrity following compression. Materials commonly employed in this capacity include starch, gelatin, sucrose, dextrose, molasses and natural and synthetic gums such as acacia, sodium alginate, carboxymethylcellulose and polyvinylpyrrolidone. The term pharmaceutical excipients as used herein also includes lubricants that improve the flow of tablet granulations and prevent adhesion of tablet material to the surfaces of tablet dies and punches. Lubricants that can be favorably employed include talc, hydrogenated vegetable oil, stearic acid and salts of stearic acid, as for example calcium stearate, magnesium stearate, aluminum stearate and zinc stearate. Also included within the scope of inert pharmaceutical agents are disintegrating agents which can be added to the tablet formulation to assist in the breakup and disintegration of the tablet following administration. Lastly, the term inert pharmaceutical excipients includes coloring agents and flavoring agents that can be added to enhance the aesthetic qualities of the tablet and make them more acceptable to the patient.

The slow release portion of the tablet comprises from about 9% to about 27% of total tablet weight of micronized nitrofurantoin and from about 8% to about 42% of total tablet weight of inert pharmaceutical excipients. Additionally, the slow release portion contains from about 14% to about 42% of total tablet weight of a pharmaceutically acceptable hydrophilic gum that provides a slow release or dissolution of the drug. The gums contained in the tablets of the present invention are intimately blended with the nitrofurantoin and other tablet excipients. On contact with aqueous fluids at body temperatures these gums become hydrated and swollen and form a gel barrier through which the drug slowly diffuses. The soft mucilaginous gum gel barrier is slowly eroded by the motion of the tablet through the gastrointestinal tract, thereby constantly exposing a fresh surface of the slow release portion of the tablet to subsequent hydration and diffusion of the drug. Naturally occurring gums such as alginic acid and tragacanth can be employed. However, the difficulty with using of naturally occurring gums is their variable gelation characteristics, due to the variable nature of the source of these materials. Preferably, pharmaceutically acceptable synthetic gums such as sodium carboxymethylcellulose, polyvinylpyrrolidone and carboxypolymethylene are employed, with the particular gum of choice employed in the preparation of the slow release portion of the tablets of the present invention being hydroxypropyl methylcellulose.

The amount of nitrofurantoin excreted in the urine during the first 2 hours following administration can be empirically correlated to the release rate of nitrofurantoin during the first hour as determined essentially using the modified in vitro dissolution test, Method II, reported in the National Formulary, XIV, pp. 893–894 (1975). Thus, a composition releasing more than 66 mg. of nitrofurantoin during the first hour of in vitro dissolution using simulated gastric fluid elicits too great an incidence of vomiting and nausea when administered to a patient. Conversely, compositions releasing less than 33 mg. of nitrofurantoin during the first hour of in vitro dissolution result in non-therapeutic urinary levels of nitrofurantoin.

The in vitro rate of nitrofurantoin dissolution can be determined as a function of the viscosity of the hydroxypropyl methylcellulose employed. High viscosities of hydroxypropyl methylcellulose within the useful concentration range release the drug too slowly and result in diminished drug absorption and efficacy. Low viscosities of hydroxypropyl methylcellulose within the useful range result in too rapid a release of the drug causing an unacceptable incidence of nausea and anorexia in the patient. In order to obtain acceptable in vitro dissolution rates of from 33 to 66 mg of nitrofurantoin released during the first hour, the hydroxypropyl methylcellulose employed must have a viscosity of from 90 to 120 cps. Example 6 illustrates the critical nature of the viscosity of hydroxypropyl methylcellulose employed in obtaining the desired release rate of nitrofurantoin from the slow release portion of the tablet of the present invention.

A preferred embodiment of the present invention comprises a layered tablet having approximately 3–4% of total tablet weight of micronized nitrofurantoin in the rapid release layer with the slow release layer having approximately 10–11% of total tablet weight of micronized nitrofurantoin with 31–32% of total tablet weight of hydroxypropyl methylcellulose having a viscosity of 100 cps., the remainder comprising inert excipients.

The tablets of the present invention are prepared in accordance with procedures well-known to the art. That is to say rapid release and slow release formulations are separately prepared and granulated. Both the rapid and slow release formulations can be either wet or dry granulated. Preferably, the rapid release portion is wet-granulated, whereas the slow release portion is processed as a dry granulation.

To prepare rapid release granules, nitrofurantoin is micronized with or without a carrier such as starch or lactose and blended with the inert pharmaceutical excipients. A granulating solution or paste, such as a 5% starch paste, is added to the resulting mixture to form the desired granules. The granules can be further subdivided by screening and placing in shallow trays and drying in an oven or other suitable drying equipment, such as a fluid bed dryer, to the desired moisture content. The dried granules may be further reduced in particle size by dry screening and are then lubricated to prevent their bridging in the granule feed hoppers or sticking to the tablet punches and dies. The granules can be lubricated by dusting or dry blending with a lubricant such as talc or zinc stearate, or they may be lubricated by spray coating.

The slow release granules are preferably prepared using a dry granulation or slugging process to better control the moisture content in this portion of the formulation and to obtain a more uniform hardness of granules. The micronized nitrofurantoin, hydroxypropyl methylcellulose and remaining inert pharmaceutical excipients are blended and pre-compressed or compacted as tablets or slugs. The compressed slugs are comminuted through the desired mesh screen, such as a U.S. Standard No. 10 or 12 screen. Alternatively, the compressed slugs can be passed through a comminuting mill and screened to the desired particle size. A lubricant is added and blended to obtain the final dry granulation.

Both rapid release and slow release granulations are fed to a tablet machine and cored or layered tablets prepared in the usual manner known to the art.

In accordance with the present invention it has been found that a layered tablet in dosage unit form containing 33 mg of nitrofurantoin in the fast release layer and 100 mg of nitrofurantoin in the slow release layer, administered two and not more than three times daily, provides comparable drug availability for a longer period of time than the currently available standard 100 mg tablet which must be administered four times daily. The term dosage unit form as used herein refers to physically discrete tablets suitable as unitary dosages for human subjects, each unit containing a predetermined quantity of active material in each of the rapid release and slow release portions of the tablet calculated to produce the desired therapeutic effect.

A comparison of the dosage unit form of the present invention with currently available nitrofurantoin capsules and tablets demonstrates a bioavailability of the drug which is equivalent to or slightly greater than that presently available, as shown in Example 5. Moreover, the administration of a single tablet in accordance with the present invention provides a more rapid onset of therapeutic efficacy and for a longer period of time than does the administration of comparable tablets of nitrofurantoin currently available as illustrated in Example 7. The amount of nitrofurantoin excreted in the urine following the administration of a single layered tablet containing 33 mg of nitrofurantoin in the rapid release layer and 100 mg of nitrofurantoin in the slow release layer averages 0.15 mg for the first half hour, an additional 1.38 mg after the first hour, 2.72 mg after 1.5 hours and 4.29 mg of nitrofurantoin after 2 hours. In contrast thereto the administration of the currently available 100 mg nitrofurantoin tablet averages only 0.07 mg for the first half hour, 0.14 mg after the first hour, 0.41 mg after 1.5 hours and 1.45 mg after 2 hours as illustrated in Example 7. Thus, the administration of a single tablet of the present invention provides both a more rapid onset and a longer period of therapeutic efficacy than has heretofore been available.

The following specific examples more particularly describe the invention described herein and are not to be construed as necessarily limiting the scope thereof.

EXAMPLE 1

Preparation of Rapid Release Granules

The following composition illustrates the preparation of sufficient rapid release granules to form the rapid release layers for 1000 layered tablets.

|  | Grams |
| --- | --- |
| Nitrofurantoin | 33 |
| Corn starch | 18.5 |
| Lactose | 48.2 |
| Zinc Stearate | 0.3 |
|  | 100.0 |

The nitrofurantoin and approximately 6 to 9 grams of the lactose is mixed and passed through a fluid energy mill or micronizer to give a particle powder size of from about 1 to 25 microns. Water, 35 ml, is added to approximately 2.0 grams of the corn starch and blended to prepare a 5% starch paste. The micronized nitrofurantoin-lactose powder, the remaining lactose and the remaining corn starch are mixed well, starch paste added and the mixture passed through a No. 12 mesh screen. The resulting granules are dried at 38° C. to a moisture content of approximately 3%. The dried granules are ground through a U.S. Standard No. 12 screen and lubricated by mixing with 0.3 grams of zinc stearate.

EXAMPLE 2

Following essentially the procedure of Example 1, rapid release granules are prepared which contain the same quantity of nitrofurantoin, but which contain additional quantities of inert pharmaceutical excipients, thereby varying the thickness of the rapid release layer in the final compressed tablet formed therefrom.

|  | Grams | Grams |
| --- | --- | --- |
| Nitrofurantoin | 33 | 33 |
| Corn Starch | 42.6 | 75.8 |
| Lactose | 123.8 | 190.3 |
| Zinc Stearate | 0.6 | 0.9 |
|  | 200.0 | 300.0 |

EXAMPLE 3

Preparation of Slow Release Granules

The compositions in Table 1 below illustrate the preparation of sufficient slow release granules to form the sustained release layers for 1000 layered tablets. All weights are expressed in grams.

Table I

| Formulation | A | B | C | D |
| --- | --- | --- | --- | --- |
| Nitrofurantoin | 100 | 100 | 100 | 100 |
| Lactose | 25 | 25 | 162 | 105.6 |
| Calcium Carbonate | 43 | — | 120 | 120 |
| Hydroxypropyl Methylcellulose (100 cps) | 84 | 126.5 | 300 | 356.4 |
| Talc | 20 | 20 | 60 | 60 |
| Zinc Stearate | 2.5 | 3 | 7.5 | 7.5 |
| Butylated Hydroxyamisole | 0.5 | 0.5 | 0.5 | 0.5 |
|  | 275.0 | 275.0 | 750.0 | 750.0 |

The nitrofurantoin and 25 grams of lactose are mixed and passed through a fluid energy mill or micronizer to give a particle size of from about 1 to 25 microns. The micronized nitrofurantoin-lactose powder, the remaining lactose, if any, the calcium carbonate, if any, the hydroxypropyl methylcellulose, the butylated hydroxyanisole antioxidant and one-half of the lubricants, talc and zinc stearate, are blended by mixing. The resulting mixture is compacted by slugging and the slugs passed through a U.S. Standard No. 12 screen. The resulting granules are lubricated by mixing with the remaining talc and zinc stearate.

EXAMPLE 4

Preparation of Layered Tablets

Slow release granules, prepared in accordance with the preceeding Example are fed into the die cavity of a Manesty Layer Press. The fill cavity is adjusted in volume to provide a bottom layer of the desired weight and the granulation is lightly tamped by subjecting to a precompression stroke. Rapid release granules, prepared in accordance with Example 1 are then fed into the same die cavity and the necessary adjustments made to provide a top layer of the desired weight. The two layers are then formed and bonded by a single compression stroke.

When prepared in this manner, the layered tablets shown in Table II below are obtained having the following characteristics. The weights indicated are expressed in milligrams.

Table II

|  | Tablet A | Tablet B | Tablet C | Tablet D |
|---|---|---|---|---|
| Rapid Release Layer | | | | |
| Total Weight Rapid Release Layer | 100 | 100 | 100 | 100 |
| Nitrofurantoin | 33 | 33 | 33 | 33 |
| Inert pharm. excipients | 67 | 67 | 67 | 67 |
| Slow Release Layer | | | | |
| Total weight Slow Release Layer | 275 | 275 | 750 | 750 |
| Nitrofurantoin | 100 | 100 | 100 | 100 |
| Hydroxypropyl methylcellulose | 84 | 126.5 | 300 | 356.4 |
| Inert pharm. excipients | 91 | 48.5 | 350 | 293.6 |
| Total weight tablet | 375 | 375 | 850 | 850 |

EXAMPLE 5

Efficacy of Layered Tablets

Single doses of the various tablet formulations prepared in Example 4 were administered to human subjects and the amounts of unchanged nitrofurantoin excreted into the urine were determined. Table III below illustrates comparison of the percent of unchanged drug recovered in the urine with commercially available nitrofurantoin macrocrystals in capsule form and nitrofurantoin tablets demonstrating a bioavailability of the drug utilizing the formulations of the present invention which is equivalent to or slightly greater than that of currently available nitrofurantoin capsules or tablets.

Table III

| Percent Unchanged Drug Recovered in Urine | | |
|---|---|---|
| Formulation | Percent (mean) | No. of Subjects |
| Tablet A | 43.8 | 12 |
| Tablet B | 36.2 | 12 |
| Tablet C | 39.7 | 12 |
| Tablet D | 34.3 | 12 |
| nitrofurantoin macrocrystals (capsules) | 34.6 | 8 |
| nitrofurantoin tablets | 37.6 | 8 |

EXAMPLE 6

The following data demonstrates that hydroxypropyl methylcellulose having a viscosity of 88 cps is unsatisfactory in controlling the release of nitrofurantoin from the slow release portion.

Following essentially the procedure of Example 3, slow release granules were prepared in accordance with Formulation C in which hydroxypropyl methylcellulose of varying viscosity was employed. The dissolution rate of nitrofurantoin was determined essentially in accordance with the standard procedure set forth in the National Formulary XIV, pp. 893–894 (1975) for Method II. Acceptable limits of nitrofurantoin released for the first hour using simulated gastric fluid range from 33 to 66 mg. Values below these limits are therapeutically ineffective, whereas values beyond these limits produce too high an incidence of side effects including nausea and anorexia. Table IV below illustrates the rate of nitrofurantoin dissolution as expressed in milligrams of nitrofurantoin.

Table IV

| Nitrofurantoin Controlled Release Tablet Dissolution | | | |
|---|---|---|---|
| Hydroxypropyl Methyl-Cellulose | 1 Hour | 3 Hours | 5 Hours |
| 88 cps | 67.53 | 39.77 | 19.33 |
| 88 cps | 68.13 | 45.17 | 10.97 |
| 88 cps | 60.27 | 46.27 | 18.43 |
| 88 cps | 67.70 | 44.53 | 9.23 |
| 88 cps | 66.13 | 42.00 | 14.30 |
| 88 cps | 67.57 | 41.67 | 15.50 |
| 107 cps | 56.1 | 37.4 | 23.6 |
| 120 cps | 39.35 | 35.24 | 24.83 |
| 120.7 cps | 49.34 | 39.06 | 26.39 |
| 120 cps | 44.84 | 37.06 | 27.01 |
| 120.7 cps | 56.77 | 43.07 | 24.48 |
| 120.7 cps | 49.00 | 32.00 | 31.00 |
| 120 cps | 44.84 | 37.06 | 27.01 |

EXAMPLE 7

Table V below illustrates the more rapid absorption and earlier onset of nitrofurantoin excretion into the urinary system using the layered tablet of the present invention as compared to currently available nitrofurantoin tablets.

Single doses of layered tablet C, prepared in accordance with the procedure of Example 4 and 100 mg nitrofurantoin tablets currently on the market were administered in a standard crossover design study to normal, healthy males and urine collected at controlled time intervals. The urine was assayed for unchanged nitrofurantoin in accordance with the procedure of Conklin and Hollifield, Clin. Chem. II, 925–931 (1965). The values are expressed in milligrams of nitrofurantoin.

Table V

| Amount (mg) of Nitrofurantoin Excreted in Human Urine During Initial 2 Hours Following Nitrofurantoin Administration | | | | | | | | |
|---|---|---|---|---|---|---|---|---|
| | Nitrofurantoin Layered Tablet C | | | | Nitrofurantoin Tablet | | | |
| Subject | 0.5 Hr | 1.0 Hr | 1.5 Hrs | 2.0 Hrs | 0.5 Hr | 1.0 Hr | 1.5 Hrs | 2.0 Hrs |
| 1 | .15 | 1.17 | 5.73 | 5.69 | 0.17 | 0.07 | 0.32 | 0.81 |
| 2 | — | — | — | — | — | — | — | — |
| 3 | .65 | 4.28 | 4.46 | 2.76 | — | — | 0.31 | 0.45 |
| 4 | .14 | 3.70 | 3.69 | 3.02 | — | 0.10 | 0.36 | 0.73 |

Table V-continued

| | Amount (mg) of Nitrofurantoin Excreted in Human Urine During Initial 2 Hours Following Nitrofurantoin Administration | | | | | | | |
|---|---|---|---|---|---|---|---|---|
| | Nitrofurantoin Layered Tablet C | | | | Nitrofurantoin Tablet | | | |
| Subject | 0.5 Hr | 1.0 Hr | 1.5 Hrs | 2.0 Hrs | 0.5 Hr | 1.0 Hr | 1.5 Hrs | 2.0 Hrs |
| 5 | .09 | .04 | .13 | .92 | 0.05 | 0.07 | 0.04 | — |
| 6 | .09 | .11 | .25 | 4.08 | 0.02 | — | — | — |
| 7 | — | — | 7.35 | 5.52 | — | — | — | 0.72 |
| 8 | .02 | .13 | .84 | 5.47 | 0.08 | 0.07 | 0.17 | 0.39 |
| 9 | .10 | 2.61 | 5.19 | 10.29 | 0.08 | 0.10 | 0.50 | 5.31 |
| 10 | .02 | .92 | .93 | 4.43 | 0.06 | 0.31 | 1.12 | 3.36 |
| 11 | .10 | .69 | .84 | 1.97 | — | — | — | 0.07 |
| 12 | — | .18 | .57 | 3.01 | 0.04 | 0.29 | 0.95 | 1.17 |
| Mean Value | 0.15 | 1.38 | 2.72 | 4.29 | 0.07 | 0.14 | 0.41 | 1.45 |

I claim:

1. A compressed pharmaceutical tablet in dosage unit form for oral administration comprising:
   a. a rapid release portion comprising from 3 to 9% of total tablet weight of micronized nitrofurantoin and from 8 to 46% of total tablet weight of inert pharmaceutical excipients; and
   b. a slow release portion comprising from 9 to 27% of total tablet weight of micronized nitrofurantoin, from 14 to 42% of total tablet weight of hydroxypropyl methylcellulose having a viscosity of from 90 to 120 cps, and from 8 to 42% of total tablet weight of inert pharmaceutical excipients.

2. A tablet in accordance with claim 1 wherein the hydroxypropyl methylcellulose has a viscosity of 100 cps.

3. A tablet in accordance with claim 1 wherein the rapid release portion and the slow release portion are in layers.

4. A layered tablet in accordance with claim 1 which contains about 3.5% of total tablet weight of micronized nitrofurantoin in the rapid release portion and the slow release portion contains about 10.5% of total tablet weight of nitrofurantoin and about 31.6% of total tablet weight of hydroxypropyl methylcellulose having a viscosity of 100 cps.

5. A method of treating urinary tract infections in humans which comprises the oral administration of a tablet of claim 1 not more than 3 times daily.

* * * * *